(12) United States Patent
Andersen et al.

(10) Patent No.: US 10,193,217 B2
(45) Date of Patent: *Jan. 29, 2019

(54) ANATOMICALLY COMPLIANT ANTENNA FOR IMPLANTABLE MEDICAL DEVICE

(71) Applicant: NeuroPace, Inc., Mountain View, CA (US)

(72) Inventors: Dean Andersen, San Jose, CA (US); Stephen T. Archer, Sunnyvale, CA (US); John Dunagan Pearson, Mountain View, CA (US)

(73) Assignee: NeuroPace, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/994,993

(22) Filed: May 31, 2018

(65) Prior Publication Data

US 2018/0277938 A1    Sep. 27, 2018

Related U.S. Application Data

(60) Continuation of application No. 15/787,713, filed on Oct. 19, 2017, now Pat. No. 10,014,571, which is a division of application No. 14/205,051, filed on Mar. 11, 2014, now Pat. No. 9,837,704.

(60) Provisional application No. 61/782,456, filed on Mar. 14, 2013.

(51) Int. Cl.
| | |
|---|---|
| *H01Q 1/27* | (2006.01) |
| *H01Q 1/40* | (2006.01) |
| *H01Q 7/00* | (2006.01) |
| *H01Q 1/36* | (2006.01) |
| *A61N 1/372* | (2006.01) |

(52) U.S. Cl.
CPC ......... *H01Q 1/273* (2013.01); *A61N 1/37229* (2013.01); *H01Q 1/36* (2013.01); *H01Q 1/40* (2013.01); *H01Q 7/00* (2013.01)

(58) Field of Classification Search
CPC .................. A61N 1/37223; A61N 1/37229
USPC ........................................... 607/60
See application file for complete search history.

(56) References Cited

U.S. PATENT DOCUMENTS

| | | |
|---|---|---|
| 6,009,350 A | 12/1999 | Renken |
| 6,016,449 A | 1/2000 | Fischell |
| 6,456,256 B1 | 9/2002 | Amundson |
| 6,490,487 B1 | 12/2002 | Kraus |
| 6,535,766 B1 | 3/2003 | Thompson |
| 6,539,253 B2 | 3/2003 | Thompson |
| 6,574,510 B2 | 6/2003 | Von Arx |
| 6,614,406 B2 | 9/2003 | Amundson |
| 6,675,045 B2 | 1/2004 | Mass |

(Continued)

*Primary Examiner* — Robert Karacsony
(74) *Attorney, Agent, or Firm* — Loza & Loza, LLP; David S. Sarisky

(57) ABSTRACT

A flexible antenna is associated with an active implantable medical device to facilitate communication between the implantable medical device and an external component in the outside world via, for example, long range or far field telemetry. The flexibility of the antenna allows it to conform to the shape of the location at which it is situated, such as on the cranial bone of a patient for an antenna associated with a cranially implanted medical device. The conformability of the antenna helps to maintain the antenna in the desired shape and to maintain it in the desired location relative to implantable medical device and the patient and improves patient comfort.

12 Claims, 4 Drawing Sheets

(56) References Cited

U.S. PATENT DOCUMENTS

| | | | |
|---|---|---|---|
| 6,690,974 B2 | 2/2004 | Archer | |
| 6,708,065 B2 | 3/2004 | Von Arx | |
| 6,809,701 B2 | 10/2004 | Amundson | |
| 6,810,285 B2 | 10/2004 | Pless | |
| 6,868,288 B2 | 3/2005 | Thompson | |
| 7,016,733 B2 | 3/2006 | Dublin | |
| 7,047,076 B1 | 5/2006 | Blaine | |
| 7,174,212 B1 | 2/2007 | Klehn | |
| 7,313,441 B2 | 12/2007 | Mass | |
| 7,319,901 B2 | 1/2008 | Dublin | |
| 7,409,245 B1 | 8/2008 | Larson | |
| 7,467,014 B2 | 12/2008 | Fuller | |
| 7,483,752 B2 | 1/2009 | Von Arx | |
| 7,554,493 B1 | 6/2009 | Rahman | |
| 7,749,265 B2 | 7/2010 | Denker | |
| 7,769,466 B2 | 8/2010 | Denker | |
| 7,826,903 B2 | 11/2010 | Denker | |
| 7,903,043 B2 | 3/2011 | Rawat | |
| 8,126,556 B2 | 2/2012 | Hjelm | |
| 8,219,205 B2 | 7/2012 | Tseng | |
| 8,239,026 B2 | 8/2012 | Dahlberg | |
| 8,301,261 B2 | 10/2012 | Bruinsma | |
| 8,321,028 B1 | 11/2012 | Thenuwara | |
| 8,538,556 B2 | 9/2013 | Keilman | |
| 9,837,704 B2 * | 12/2017 | Andersen | H01Q 1/273 |
| 2005/0203584 A1 | 9/2005 | Twetan et al. | |
| 2008/0300660 A1 | 12/2008 | John | |
| 2009/0248105 A1 | 10/2009 | Keilman et al. | |
| 2010/0114245 A1 | 5/2010 | Yamamoto et al. | |
| 2011/0009925 A1 | 1/2011 | Leigh | |
| 2011/0137380 A1 | 6/2011 | Tseng et al. | |

* cited by examiner

ANATOMICALLY COMPLIANT ANTENNA FOR IMPLANTABLE MEDICAL DEVICE

CROSS-REFERENCE TO RELATED APPLICATION(S)

This application is a continuation of U.S. application Ser. No. 15/787,713, filed on Oct. 19, 2017, entitled "Anatomically Compliant Antenna for Implantable Medical Device," now U.S. Pat. No. 10,014,571, which is a divisional of U.S. application Ser. No. 14/205,051, filed on Mar. 11, 2014, entitled "Anatomically Compliant Antenna for Implantable Medical Device," now U.S. Pat. No. 9,837,704, which claims the benefit of U.S. Provisional Application Ser. No. 61/782,456 entitled "Anatomically Compliant Antenna for Implantable Medical Device," filed Mar. 14, 2013, which is expressly incorporated by reference herein in its entirety.

BACKGROUND

Field

The present technology relates generally to antennas associated with an implantable medical device for communication between the implantable medical device and one or more external components in the outside world, such as via telemetry.

Background

Active implantable medical devices are known that can be configured to communicate with external components wirelessly, such as via a form of telemetry. The communication may be desirable to, for example, download information acquired by and stored on the implanted medical device to an external component, such as patient-controlled external component. Alternatively or additionally, an external component configured as a "programmer" selectively may be brought into communication with the implantable medical device to download data from the implant or to send data to the implant from the programmer, such as new programming instructions that control whatever it may be that the implantable medical device is configured to do (e.g., measure electrographic signals from the patient and/or "detect events" (such as patterns) whenever they occur in the signals, or deliver a form of electrical stimulation to the patient).

A communication link between the implantable medical device and an external component may be established with an intermediate device, such as wand for near-field or short-range telemetry. For example, the implantable medical device may be associated with a telemetry coil (which may be situated outside of the implant's housing) which enables transmission and reception of signals, to or from an external apparatus, via inductive coupling. Alternatively, a communication link between the implant and an external component may be established with an antenna for a radio frequency (RF) link. Far field or long-range telemetry may obviate the need for the intermediate device (e.g., the wand) and allow the external component to be further away from the implantable medical device than is the case with near field telemetry when a communications link is established.

SUMMARY

An antenna for facilitating communication between an implanted medical device and external component includes a length of flexible metal shaped into a plurality of turns. The shaped metal is arranged to be located alongside the housing of an implantable medical device. A strain relief configured to be connected to the housing encases the length of flexible metal. The antenna is suitable for enabling communication between the implantable medical device and an external component via long range telemetry.

Another antenna for facilitating communication between an implanted medical device and external component also includes a length of flexible metal shaped into a plurality of turns and arranged to be located alongside the housing of an implantable medical device. This antenna includes an encasement for the length of flexible metal to entirely contain the flexible metal within its boundaries. The encasement is disposed so that when connected to the housing, the encasement will lie alongside a portion of the housing.

An implantable medical device includes a housing and an antenna feedthrough extending from the housing. The device also includes an antenna coupled to the antenna feedthrough. The antenna is configured to be bent and, upon being bent, to retain a bent shape. The antenna may be encased in an encasement that lies along a side of the housing, or in a strain relief connected to the housing.

BRIEF DESCRIPTION OF THE DRAWINGS

The accompanying drawings, which are incorporated in and form a part of this specification, illustrate and serve to explain the principles of embodiments in conjunction with the description. Unless specifically noted, the drawings referred to in this description should be understood as not being drawn to scale.

DETAILED DESCRIPTION

Figure 1:
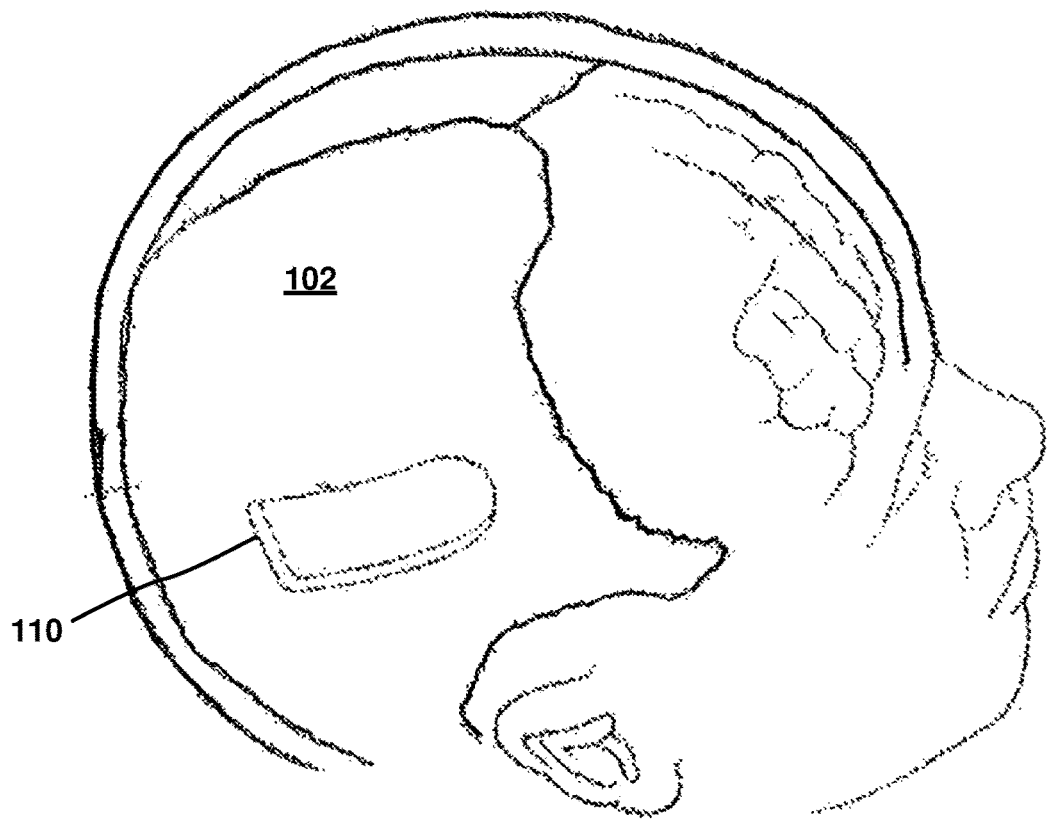
FIG. 1 is a schematic view of a patient's skull in which a craniectomy has been performed to create a fenestration or hole in which to implant a medical device.

Various aspects of the disclosure will be described more fully hereinafter with reference to the accompanying drawings. This disclosure may, however, be embodied in many different forms by those skilled in the art and should not be construed as limited to any specific structure or function presented herein. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of this disclosure, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure and/or functionality in addition to or instead of other aspects of this disclosure.

It should be understood that any aspect of the disclosure disclosed herein may be embodied by one or more elements of a claim.

An implantable medical device system may include implantable components including one or more electrode-bearing brain leads for delivering stimulation to (or for sensing field potential measurements from) neural tissue, and an active implantable medical device configured to deliver stimulation signals through the electrodes and leads and/or to receive and process physiological signals sensed by the electrodes from the patient (e.g., EEG signals). The lead(s) may be connected to the neurostimulator at a lead connector associated with a housing of the neurostimulator.

External components of an implantable neurostimulation system may include a "programmer" that a user/physician can use to communicate bidirectionally with the implantable medical device (e.g., to program the implant with parameters that govern what stimulation waveforms the implant will generate and when it will generate them and through which electrodes the stimulation waveforms will be delivered). The programmer and implant also may be configured so that information acquired by and/or stored in a memory of the implant can be downloaded to the programmer for analysis by a physician. An additional external component may include a patient remote monitor, which may be configured for one-way communication with the implant (e.g., to download data from the implant onto the patient remote monitor). Another external component may include a central database with which the programmer and any patient remote monitor can be networked. A responsive neurostimulation system manufactured under the tradename "RNS SYSTEM" by NeuroPace, Inc. is an example of such an implantable medical device system.

Implantable medical device systems including a cranially-implanted component also are described in, for example, U.S. Pat. No. 6,016,449 to Fischell, et al. for "System for Treatment of Neurological Disorders", issued Jan. 18, 2000, U.S. Pat. No. 6,810,285 to Pless et al. for "Seizure Sensing and Detection Using An Implantable Device," issued Oct. 24, 2004, and U.S. Pat. No. 6,690,974 to Archer et al. for "Stimulation Signal Generator for an Implantable Device" issued Feb. 10, 2004. Each of the '449, '285 and '974 patents is hereby incorporated by reference in the entirety.

Disclosed herein is a pliable, flexible antenna for use in implantable long-range communication. The antenna is configured to be manipulated, e.g., bent, to conform to the human anatomy and once bent, to retain it shape. The antenna may be housed in a flexible elastomer bio-compatible material, such as silicone. The antenna may be made from thin bio-compatible electrically conductive metal and thus may have metallic properties such as bending and shape retention. When placed in, on, or around the cranium, the antenna may be pressed into position relative to the cranium and conformed to the anatomy. Because of the material properties of the antenna, the antenna holds or retains a shape that conforms to the part of the body, e.g., the cranium, where the antenna is situated. This is important since the curvature of the cranium can change depending on the age of the patient or upon the location on the cranium at which the device is implanted. The more forming and compliant the antenna material, the more comfortable the implanted antenna will be for the patient.

Long-range (wireless) telemetry is an emerging form of communication between implantable medical devices (IMD) and external programmers and monitors. This communication can take place over several meters or even across rooms. Previous generation of systems used near-field inductive telemetry to communicate from implanted device to external programmer. In modern and emerging systems, radio frequencies are used for long-range telemetry allowing much longer distances of communication. Along with radio frequencies comes the demand for better, high-tuned antennas to support long-range telemetry.

An international standard for implant communication is the Medical Implant Communication Service) MICS, which operates at 401-406 MHz [ETSI, 2002]. Due to the frequency of this signal and the limited power restrictions imposed by the standard, antennas used for this communication must reside outside of the protective metal housing used in most IMDs.

Most antenna designs for IMDs are placed just outside the metal housing but within rigid encapsulation, such as epoxy, to keep the antenna structure rigid and immobile. Often this is desirable since the shape and length of the antenna can have a profound effect on the performance of the antenna. The main criterion for the performance of an antenna is its efficiency in converting electrical current into electromagnetic power. The antenna is connected to the internal hermetically sealed electronics by an insulator-to-metal feedthrough (where the insulator may be formed of a material such as a ceramic or glass). Feedthrough structures bridge the hermetic barrier.

Cochlear implants are a type of medical implant that is implanted subcutaneous on top of the cranium. Cochlear implants have antennas for coupling power to the implant as well as transmitting and receiving data. Typically, many turns of wire are housed in a semi-rigid structure to increase the coupling efficiency for power transfer. The semi-rigid structure is often made from silicone elastomer. The number of turns of wire makes the antenna pliable; however, the antenna does not hold its shape upon flexing.

To ready a patient for a medical device to be implanted in the cranium, and referring now to FIG. 1, a craniectomy may be performed to remove a portion of the bone in the patient's cranium 102. The medical device may be intended to be implanted in the hole or fenestration 110 left behind after the removal of the bone.

Figure 2:
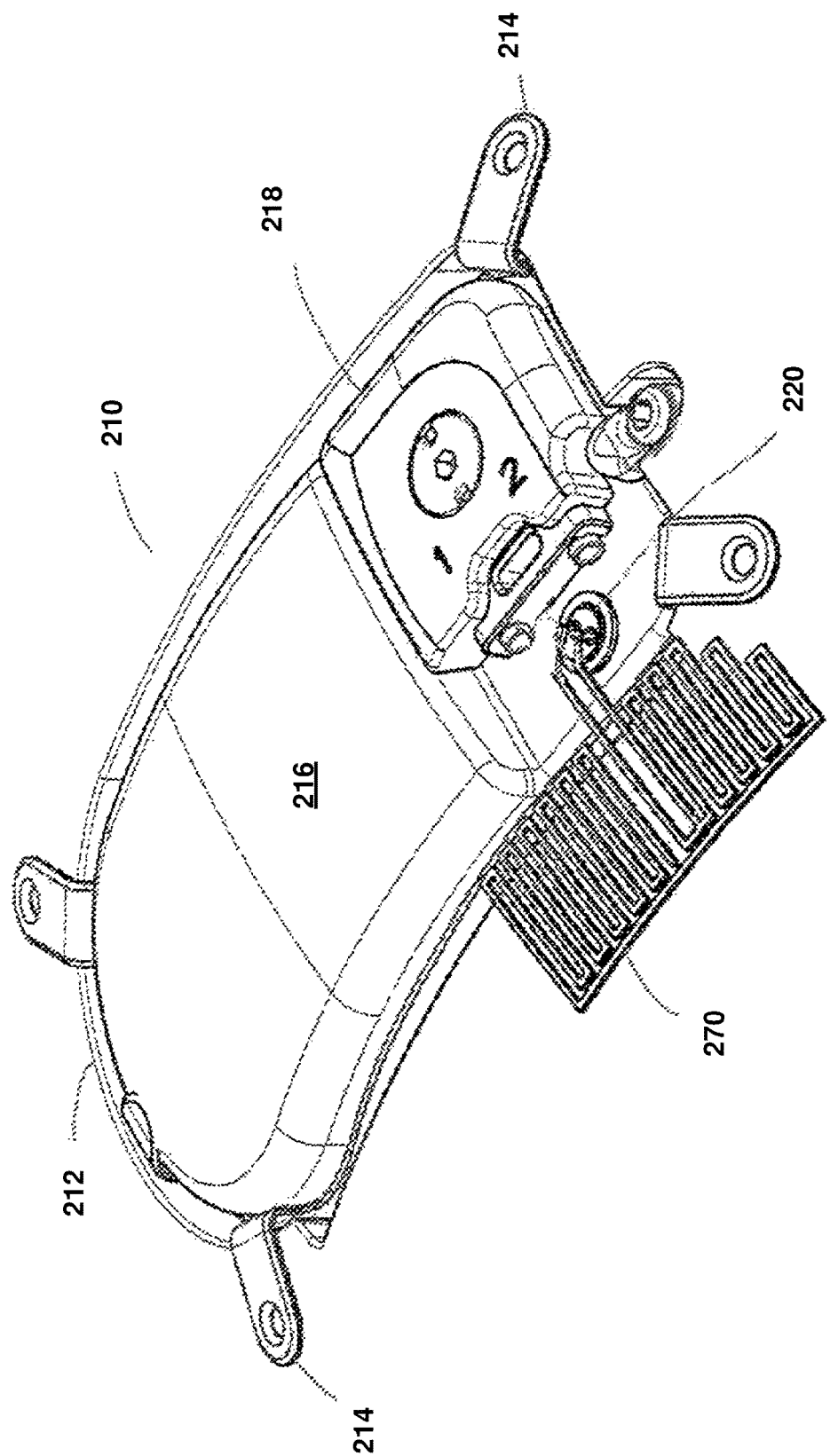
FIG. 2 is a perspective view of an active implantable medical device provided with a device housing associated with an antenna.

FIG. 2 shows an active implantable medical device 210 in the form of an implantable neurostimulator. The neurostimulator is situated in a tray or ferrule 212 which is provided with tabs 214 for receiving bone screws or other bone-attaching elements to secure the ferrule to the patient's cranial bone (not shown). The ferrule 212 may be installed in a hole 110 formed in the patient's skull (e.g., via a craniectomy), as shown in FIG. 1.

The neurostimulator 210 comprises a housing 216 which may be made of a conductive biocompatible material such as titanium. The housing 216 may house electronics including a CPU and various subsystems that are configured to, for example, monitor physiological signals received by the implantable medical device and process and condition the signals (e.g., filter and amplify and/or digitize the signals); apply one or more algorithms such as "detection tools" to the signals in order to try to detect one or more patterns or predetermined "events" occurring in the signal that may be associated with a neurological disorder, such as epileptic seizures; store portions of signals in a memory of the implant whenever an event is detected or otherwise when commanded to do so; store information about the device relevant to the device's behavior or a state of the device (e.g., information relating to when amplifiers of the device are saturated or how much life remains in the implant's battery); and generate and deliver electrical stimulation signals to the patient, for example, in response to the detection of an event.

Responsive neurostimulation systems are described in, for example, U.S. Pat. No. 6,016,449 to Fischell, et al. for "System for Treatment of Neurological Disorders", issued Jan. 18, 2000, U.S. Pat. No. 6,810,285 to Pless et al. for "Seizure Sensing and Detection Using an Implantable Device," issued Oct. 24, 2004, and U.S. Pat. No. 6,690,974 to Archer et al. for "Stimulation Signal Generator for an Implantable Device" issued Feb. 10, 2004. Each of the '449, '285 and '974 patents is hereby incorporated by reference in the entirety.

The neurostimulator 210 may be configured to connect via a lead connector 218 to one or more brain leads (not shown) that are capable of sensing physiological information from (e.g., EEG information as field potential measurements) and/or delivering a form of neuromodulation to (e.g., current-regulated or voltage-regulated electrical stimulation) the patient. For example, the lead connector 218 shown in FIGS. 2-4 is labeled "1" and "2" to guide a surgeon as to where to connect one or two brain leads.

In FIG. 2, a flexible antenna 270 is shown configured from one or more lengths of wire or other lengths of metal characterized by a rectangular cross section. The one or more wires are arranged to form a series of narrow, interconnected rectangular curves extending outward from the edge of the housing 216. The series of rectangular curves defines the overall configuration of the flexible antenna 270. The properties of the material from which the antenna 270 is formed allow the antenna to be bent and formed so as to change the overall configuration of the antenna. For example, an original overall configuration of the antenna 270 may resemble a substantially flat rectangle. Upon implant and bending of the antenna, the overall configuration may assume an curved or arced rectangular form.

Once the flexible antenna 270 is formed into the desired shape, it will tend to stay in that shape by virtue of the properties of the material from which it is formed (i.e., metal). The antenna 270 is connected to the implantable neurostimulator housing 216 at an antenna feedthrough 220. The antenna feedthrough 220 provides a pair of connections (e.g., terminals) to electrically connect the antenna to an "antenna" and a "reference" line within a circuit located inside the housing 216. (The interior of the housing may be hermetically sealed from the exterior of the housing to discourage bodily fluids or tissue from getting inside the housing.)

Figure 3:
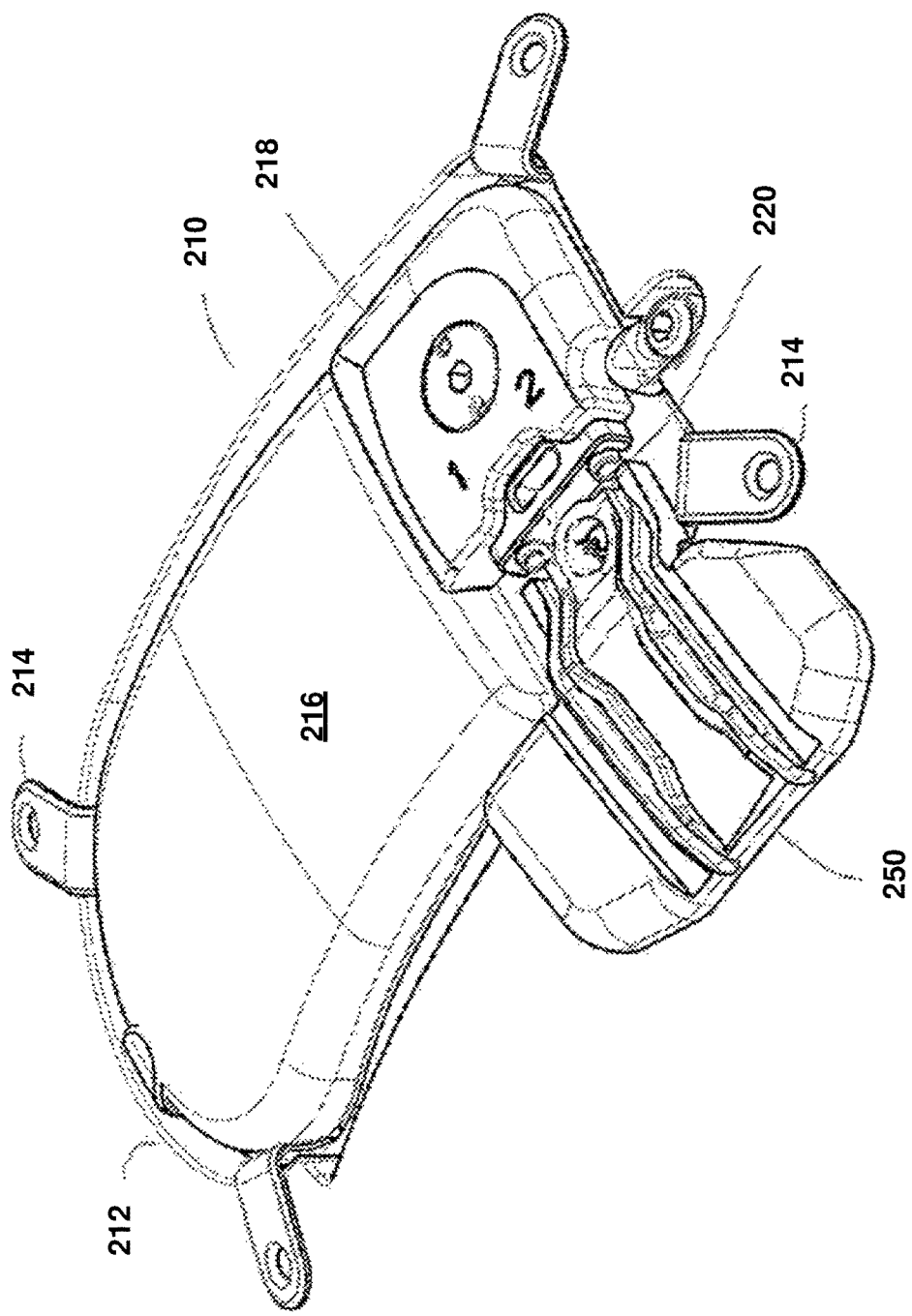
FIG. 3 is a perspective view of another active implantable medical device provided with a device housing associated with an antenna.
Figure 4:
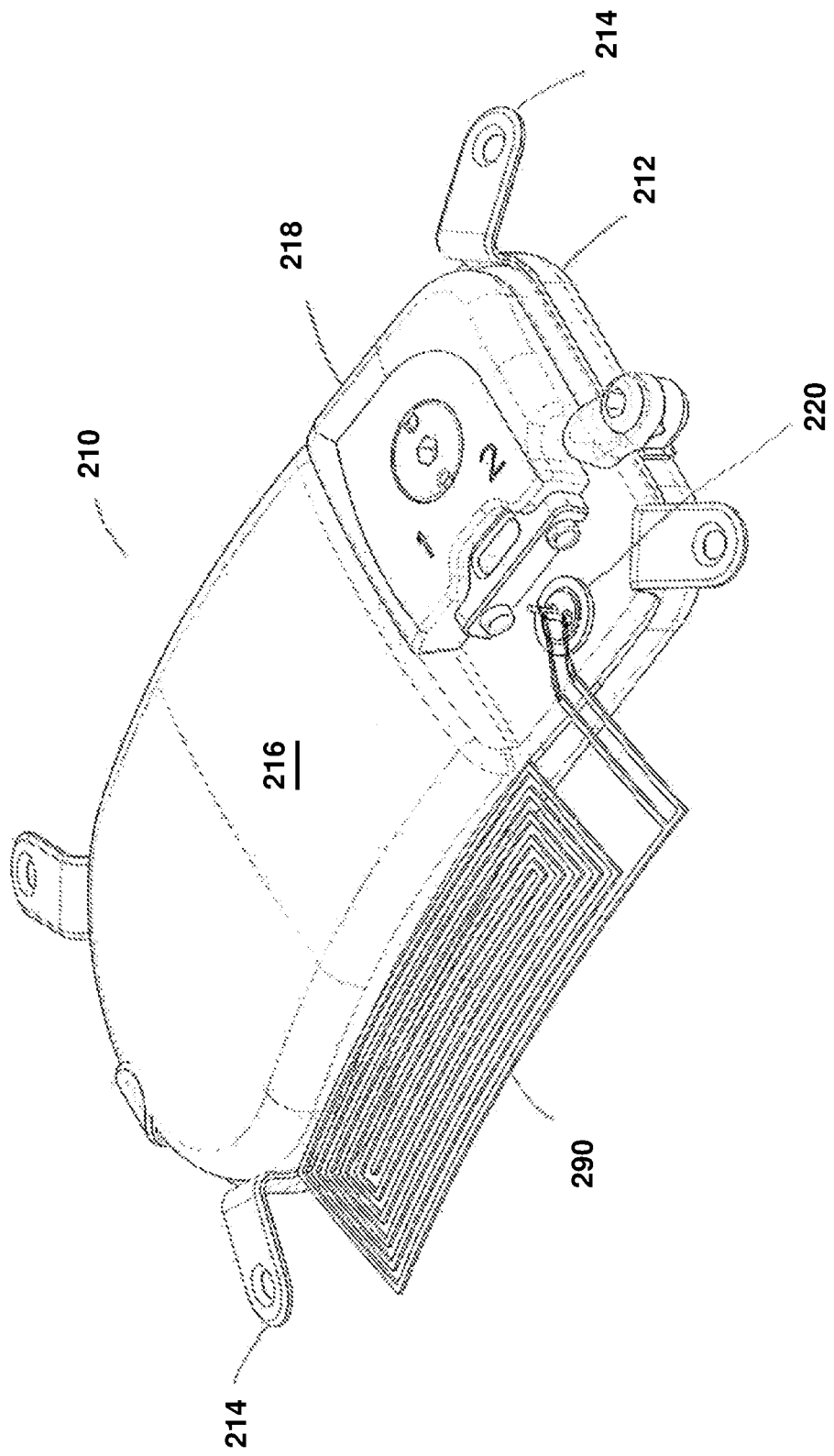
FIG. 4 is a perspective view of another an active implantable medical device provided with a device housing associated with an antenna.

In some embodiments, and with reference now to FIG. 3, a strain relief 250 is provided near the points where the proximal end of each brain lead is connected at the lead connector 218 to the implantable medical device housing 216. As its name suggests, the strain relief 250 may reduce strain on the proximal lead ends where the leads connect to the device. The strain relief 250 may be formed from a pliable or resilient material such as silicone. The strain relief 250 may be connected to the housing 216.

In FIG. 3, the strain relief 250 is configured to fit a flexible antenna similar to the flexible antenna 270 described with reference to FIG. 2 within it. More particularly, the strain relief 250 of FIG. 3 is dimensioned so that the antenna 270 will fit entirely within in it, such as the antenna being fully encased in the material of the strain relief 250 or the antenna being included in a hollow portion (not shown) of the strain relief. Desirably, the material from which the strain relief 250 is formed is flexible and/or pliant, so that both the strain relief and the flexible and/or pliant antenna provided within the strain relief, will conform to the contours of the patient's cranium and will be comfortable for the patient.

FIG. 4 is an alternate embodiment of an antenna 290 associated with an implantable medical device housing 216. The flexible antenna 290 extends alongside a length of the housing 216. The antenna 290 is formed of one or more wires arranged to form a rectangular spiral. The rectangular spiral defines the overall configuration of the flexible antenna 290. The properties of the material from which the antenna 290 is formed allow the antenna to be bent and formed so as to change the overall configuration of the antenna. For example, an original overall configuration of the antenna 290 may resemble a substantially flat rectangle. Upon implant and bending of the antenna, the overall configuration may assume a curved or arced rectangular form.

The antenna 290 may be in operable communication with the electronics inside the housing 216 via the antenna feedthrough 220. The antenna 290 may be encased in resilient conformable material (not shown) defining an encasement. The encasement may be formed of silicone or an epoxy or like material. The encasement may be disposed so that when connected to the housing, the encasement will lie alongside a portion of the housing.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An implantable medical device configured to be implanted in a patient, comprising:
   a housing configured for placement in a hole formed in a cranium of the patient; and
   an antenna positioned relative to the housing such that: 1) a side edge of the antenna is adjacent to and extends substantially parallel to and along an edge of the housing, and 2) upon placement of the housing in the hole, the antenna is positioned outside of the hole, adjacent a surface of the cranium,
   wherein the antenna is configured so that at implant of the implantable medical device in the patient, the antenna is capable of being bent to conform to an anatomical contour of the patient and, upon being bent, is capable of retaining a bent shape.

2. The implantable medical device of claim 1, further comprising a strain relief configured to be connected to the housing and to encase the antenna.

3. The implantable medical device of claim 2, wherein the strain relief comprises a hollow interior portion within which the antenna is encased.

4. The implantable medical device of claim 2, wherein the strain relief is formed of a material and the antenna is fully encased in the material.

5. The implantable medical device of claim 2, wherein the strain relief is configured to support leads extending from the housing.

6. The implantable medical device of claim 2, wherein the strain relief is formed from a flexible elastomer material.

7. The implantable medical device of claim 1, wherein the antenna comprises a length of flexible metal shaped into a plurality of turns that form a geometric configuration.

8. The implantable medical device of claim 7, wherein the length of flexible metal shaped into a plurality of turns is configured to be bent from a first shape of the geometric configuration that is substantially flat, to a second shape of the geometric configuration that is curved, wherein the second shape corresponds to the bent shape.

9. The implantable medical device of claim 8, wherein the geometric configuration is rectangular.

10. The implantable medical device of claim 9, wherein the plurality of turns of the length of flexible metal form a rectangular spiral.

11. The implantable medical device of claim 9, wherein the plurality of turns of the length of flexible metal form a series of interconnected rectangular curves.

12. The implantable medical device of claim 1, further comprising a lead connector structure having connector ports configured to connect with at least one lead, and wherein the antenna is structurally independent of the lead connector structure.

\* \* \* \* \*